(12) United States Patent
Scarberry et al.

(10) Patent No.: US 6,877,513 B2
(45) Date of Patent: Apr. 12, 2005

(54) INTRAORAL APPARATUS FOR ENHANCING AIRWAY PATENCY

(75) Inventors: Eugene N. Scarberry, Trafford, PA (US); Eric W. Starr, Allison Park, PA (US); Shari Barnett, Wexford, PA (US); Robert R. Rogers, Wexford, PA (US); Lance Busch, Trafford, PA (US)

(73) Assignee: Respironics, Inc., Murrysville, PA (US)

( * ) Notice: Subject to any disclaimer, the term of this patent is extended or adjusted under 35 U.S.C. 154(b) by 311 days.

(21) Appl. No.: 09/761,789

(22) Filed: Jan. 17, 2001

(65) Prior Publication Data

US 2001/0047805 A1 Dec. 6, 2001

Related U.S. Application Data

(60) Provisional application No. 60/117,489, filed on Jan. 21, 2000.

(51) Int. Cl.$^7$ ............................. A61F 5/56; A61M 16/00
(52) U.S. Cl. ....................... 128/848; 128/859; 128/860; 128/200.24; 602/902
(58) Field of Search .................................. 128/848, 859, 128/860, 207.14; 482/13; 433/6, 140; 602/902

(56) References Cited

U.S. PATENT DOCUMENTS

| | | |
|---|---|---|
| 1,990,411 A | 8/1931 | Lowry |
| 2,705,006 A | 3/1955 | Cettel et al. |
| 2,711,730 A | 6/1955 | Rogers |
| 3,132,647 A | 5/1964 | Corniello |
| 3,297,021 A | 1/1967 | Davis et al. |
| 3,312,216 A | 4/1967 | Wallshein |
| 3,312,217 A | 4/1967 | McKinstry |
| 3,884,226 A | 5/1975 | Tepper |
| 3,998,209 A | 12/1976 | Macvaugh |
| 4,169,473 A | 10/1979 | Samelson |
| 4,196,724 A | 4/1980 | Wirt et al. |
| 4,220,142 A | 9/1980 | Rosen et al. |
| 4,304,227 A | 12/1981 | Samelson |

(Continued)

FOREIGN PATENT DOCUMENTS

| | | |
|---|---|---|
| DE | 65194 | 11/1892 |
| DE | 4026602 C1 | 8/1990 |
| EP | 2 320 501 | 4/1973 |
| EP | 0 182 387 | 11/1985 |
| EP | 0 264 516 | 10/1986 |
| EP | 0 487 469 A1 | 11/1991 |
| GB | 874480 | 9/1957 |
| WO | WO 92/05752 | 4/1992 |
| WO | WO 00/76431 A1 | 12/2000 |

OTHER PUBLICATIONS

Lowe, et al., "Effects of a Mandibular Repositioning Appliance Used in the Treatment of Obstructive Sleep Apnea on Tongue Muscle Activity", 1990 Wiley–Liss, Inc., Sleep and Respiration, pp. 395–405.
Toone, "SNOAR No More", 1987, Brochure.
Meade, "Snore Guard, Questions and Answers on Snoring and Sleep Apnea", no date, Brochure.
George, "A Modified Functional Appliance for Treatment of Obstructive Sleep Apnea", Journal of Clinical Orthodontics, 1987, Article.
Paskow, et al., "Dentistry's Role in Treating Sleep Apnea and Snoring", 1991, Dentistry Paper.
Lowe, "Three–Dimensional Evaluations of Tongue and Airway Size Overview", Association of Professional Sleep Societies, Arizona, 1992, Pre–Meeting Course.

*Primary Examiner*—Henry Bennett
*Assistant Examiner*—Mital Patel
(74) *Attorney, Agent, or Firm*—Michael W. Haas

(57) ABSTRACT

An apparatus for selectively positioning intraoral anatomic features of a human patient to enhance upper airway stability for use alone or in combination with positive airway pressure as therapeutic treatment for obstructive sleep apnea and other conditions, such as snoring, which are symptomatic of upper airway instability.

18 Claims, 8 Drawing Sheets

U.S. PATENT DOCUMENTS

| | | |
|---|---|---|
| 4,386,405 A | 5/1983 | Lewin et al. |
| 4,593,686 A | 6/1986 | Lloyd et al. |
| 4,669,459 A | 6/1987 | Spiewak et al. |
| 4,676,240 A | 6/1987 | Gardy |
| 4,715,368 A | 12/1987 | George |
| 4,859,181 A | 8/1989 | Neumeyer |
| 4,901,737 A | 2/1990 | Toone |
| 4,932,867 A | 6/1990 | Ueno |
| 4,976,618 A | 12/1990 | Anderson |
| 4,981,437 A | 1/1991 | Wilcox |
| 5,018,533 A | 5/1991 | Hawkins |
| 5,042,506 A | 8/1991 | Liberati |
| 5,046,512 A | 9/1991 | Murchie |
| 5,052,409 A | 10/1991 | Tepper |
| 5,056,534 A | 10/1991 | Wright |
| 5,092,346 A | 3/1992 | Hays et al. |
| 5,154,184 A | 10/1992 | Alvarez |
| 5,316,020 A | 5/1994 | Truffer |
| 5,373,859 A | 12/1994 | Forney |
| 5,409,017 A | 4/1995 | Lowe |
| 5,465,734 A | 11/1995 | Alvarez et al. |
| 5,537,994 A | 7/1996 | Thornton |
| 5,649,540 A | 7/1997 | Alvarez et al. |
| 5,826,579 A | 10/1998 | Remmers et al. |
| 5,861,001 A | 1/1999 | Katsev |
| 5,868,138 A | 2/1999 | Halstrom |
| 5,884,625 A | 3/1999 | Hart |
| 5,884,628 A | 3/1999 | Hilsen |
| 5,915,385 A | 6/1999 | Hakimi |
| 5,921,240 A | 7/1999 | Gall |
| 5,921,241 A | 7/1999 | Belfer |
| 5,921,942 A | 7/1999 | Remmers et al. |
| 5,941,247 A | 8/1999 | Keane |
| 5,954,048 A | 9/1999 | Thornton |
| 5,983,892 A | 11/1999 | Thornton |
| 6,089,232 A | 7/2000 | Portnoy et al. |
| 6,092,523 A | 7/2000 | Belfer |
| 6,109,265 A | 8/2000 | Frantz et al. |
| 6,129,084 A | 10/2000 | Bergersen |
| 6,155,262 A | 12/2000 | Thornton et al. |
| 6,161,542 A | 12/2000 | Halstrom |
| 6,170,485 B1 | 1/2001 | Orrico |
| 6,408,851 B1 | 6/2002 | Karell |

INTRAORAL APPARATUS FOR ENHANCING AIRWAY PATENCY

CROSS REFERENCE TO RELATED APPLICATIONS

This application claims priority under 35 U.S.C. 0 119(e) from provisional U.S. patent application No. 60/117,489, filed Jan. 21, 2000, the contents of which are incorporated herein by reference.

BACKGROUND OF THE INVENTION

1. Field of the Invention

The present invention pertains to an apparatus for enhancing the patency of a patient's upper airway, and, in particular, an apparatus for stabilizing anatomical features associated with the upper airway so as to minimize airway obstruction or restriction. The invention further pertains to an intraoral apparatus having selectively adjustable moving members for optimally positioning various anatomical features associated with the upper airway for optimal upper airway stability, and to a system using such intraoral apparatus, alone or in combination with positive airway pressure or ventilation, as a therapeutic treatment for upper airway instability.

2. Description of the Related Art

Although upper airway stabilization can be used in a wide range of medical applications, the following description discusses the invention as a treatment for obstructive sleep apnea, hypopnea, and upper airway resistance syndrome. Obstructive sleep apnea or OSA, obstructive sleep hypopnea, and upper airway resistance syndrome (UARS) are among a variety of known disorders characterized by episodes of complete or partial upper airway obstruction during a state of diminished consciousness, such as sleep, anesthetization, or post anesthesia. OSA, hypopnea, and UARS cause intermittent interruption of ventilation during sleep with the consequence of potentially severe oxyhemoglobin desaturation. Typically, those afflicted with OSA, hypopnea, and UARS experience repeated, frequent arousal from sleep in response to the oxygen deprivation. The arousals result in sleep fragmentation and poor sleep continuity.

Consequences of OSA, hypopnea, and UARS may include debilitating daytime sleepiness and cognitive dysfunction, systemic hypertension, cardiac dysrythmias, pulmonary artery hypertension and congestive heart failure. Other consequences may include a predisposition to myocardial infarction, angina pectoris, stroke, right ventricular dysfunction with cor pulmonale, carbon dioxide retention during wakefulness as well as during sleep, and continuous, reduced arterial oxygen tension. Moreover, the cognitive impairment resulting from OSA, hypopnea, and UARS puts those afflicted at elevated risk of accidents.

The pathogenesis of the airway obstruction that characterizes OSA, hypopnea, and UARS can include both anatomic and functional abnormalities of the upper airway that result in increased air flow resistance. Such abnormalities may include narrowing of the upper airway due to suction forces created during inspiration, the effect of gravity pulling the tongue back to appose the pharyngeal wall, and insufficient muscle tone in the upper airway dilator muscles, among others. It is also believed that excessive soft tissue in the anterior and lateral neck, as commonly observed in obese persons, can apply sufficient pressure to internal structures to narrow the upper airway and restrict air flow.

Conventional treatment of OSA, hypopnea, and UARS has included surgical intervention, such as uvalopalotopharyngoplasty, gastric surgery for obesity, mandibular advancement procedures, maxillo-facial reconstruction, and tracheostomy. However, surgery potentially involves considerable risk of post-operative morbidity and mortality. In addition, the failure rate of surgery is disturbingly high. Pharmacological therapy has also been proposed to treat OSA, hypopnea, and UARS; however, results have been generally disappointing.

More recently, continuous positive airway pressure (CPAP) or bi-level positive airway pressure applied during sleep has been used to treat OSA, hypopnea, and UARS patients. Positive pressure is applied in the upper airway to splint or support the airway, thereby preventing its collapse and the resultant airway obstruction. Although positive airway pressure can nearly always stabilize the upper airway, in some cases the required pressure magnitude is unacceptable for other reasons. For example, positive airway pressure may adversely affect spontaneous patient respiration, or may not be well tolerated by the patient.

The prior art is also replete with disclosures of intraorally fitted appliances, including U.S. Pat. Nos. 4,981,437 and 4,932,867, that disclose a method and apparatus for constructing dentures, which are useful, for example, in treating breathing disorders. U.S. Pat. No. 4,386,405 discloses a device for measuring the location, attitude, or change of location of a patient's lower jaw. U.S. Pat. No. 4,859,181 relates to optical measurement of jaw movement. U.S. Pat. Nos. 3,998,209 and 4,220,142 disclose conditioning systems for use in a program of behavior modification to eliminate snoring, while U.S. Pat. No. 4,976,618 relates to treatment of temporomandibular joint dysfunction and bruxism. U.S. Pat. No. 3,297,021 discloses an intraoral strain gauge and telemetering of information from an intraoral location to an outside indicator.

U.S. Pat. No. 5,018,533 purports to disclose a process for reducing the occurrence of apneic episodes for persons with no teeth. U.S. Pat. No. 4,901,737 purports to disclose apparatus and method for repositioning the mandible in an inferior or open, and anterior or protrusive position as compared to the normal closed position of the jaw. In general, lower jaw or mandible positioning devices are known, although not necessarily for OSA, hypopnea, and UARS treatment.

The following U.S. patents purport to relate to tongue positioning and/or retaining apparatus: U.S. Pat. Nos. 5,154,184, 5,092,346, 5,046,512, 4,676,240, 4,169,473, 4,304,227 and 4,593,686. Other patents addressing the matter of tongue positioning include the following: U.S. Pat. Nos. 5,649,540, 5,465,734, 5,373,859, 5,052,409, 4,715,368, 4,196,724, 3,884,226, 3,312,216 and 3,132,647, as well as European patent 0182387 and British patent 874,480. The following patents purport to relate to chin straps or similar apparatus intended to hold the jaw closed: U.S. Pat. Nos. 3,312,217, 2,711,730 and 1,990,411.

Still other patents relate to apparatus for interaction with the soft palate in the user's oral cavity. These include U.S. Pat. No. 4,669,459 and 5,316,020, German patent no. DE 40 26 602 and European patent no. EP 0264516. Other patents of general interest include U.S. Pat. No. 5,056,534 and 2,705,006, German patent nos. 65194 and 2320501, and PCT publication no. WO 92/05752 and European patent application no. 0 487 469 A1.

While the above-identified conventional devices and techniques are purported to treat upper airway instability, such as OSA or snoring, they are successful, if at all, in only a limited pool of patients or under limited circumstances. Therefore, there remains a relatively large number of patients who's airway disorder is believed to be treatable using an intraoral appliance, yet conventional appliances are ineffective, overly burdensome, uncomfortable, or any combination thereof.

SUMMARY OF THE INVENTION

Accordingly, it is an object of the present invention to provide an apparatus for enhancing upper airway stability that overcome the disadvantages associated with conventional intraoral appliances. More specifically, the invention contemplates a novel and improved apparatus for treatment of OSA, hypopnea, UARS and other conditions by retaining, in a preferred position, one or more anatomic features of the patient associated with the upper airway from the group including the tongue and the soft palate, alone or in combination with the application of a positive pressure, such as CPAP or bi-level pressure, in the patient's upper airway. The present invention further contemplates a novel and improved apparatus for treatment of OSA and other conditions by retaining, in a preferred position, the mandible or lower jaw in combination with the application of a positive pressure, such as CPAP, in the patient's upper airway. The combination of a positive pressure airway splint and mechanical positioning of selected intraoral features produces enhanced upper airway patency, thus providing an effective treatment for OSA, hypopnea, and UARS, as well as other conditions associated with upper airway instability. In addition, the patient interface appliance of the present invention provides an interface for providing positive pressure support for a patient needing positive pressure assistance to breathing, and who do not have upper airway instability.

The proposed mechanical positioning or retention of the tongue or soft palate may be sufficient, without a positive pressure support therapy, to provide the requisite upper airway stability for prevention of airway obstruction or restriction. This can be of considerable benefit to those patients who do not tolerate CPAP therapy, for example. However, even if mechanical positioning of the tongue or soft palate is by itself insufficient to eliminate the airway obstruction or restriction, the same in combination with application of pressure support therapy, such as CPAP or bi-level pressure support, at a lower pressure than would otherwise be required, will eliminate the obstructive/restrictive episodes in many patients. Hence, the potential beneficiaries of the present invention include not only patients who do not tolerate CPAP therapy at all, but also those who tolerate CPAP therapy up to a critical positive pressure, but are unable to tolerate higher CPAP pressures. The anatomic feature positioning include tongue positioning, soft palate tissue distension, alone or in combination with lower jaw positioning and stabilization. It should be noted that the benefits of the oral appliance of the present invention, i.e., to enable reduced pressure levels for the pressure support therapy, are applicable not only to patients suffering from OSA, hypopnea, UARS, and other conditions associated with upper airway instability, but also to any patient receiving a pressure support therapy for any reason.

These and other objects, features and characteristics of the present invention, as well as the methods of operation and functions of the related elements of structure and the combination of parts and economies of manufacture, will be more apparent upon consideration of the following detailed description and the appended claims, with reference to the accompanying drawings, all of which form a part of this specification, wherein like reference numerals designate corresponding parts in the various figures. It is to be expressly understood, however, that the drawings are for the purpose of illustration and description only and are not intended define the limits of the invention. Nor is the size or scale of any elements shown in the drawings intended to reflect actual size, scale or proportion. In addition, the method of the invention includes any description herein of how the described apparatus functions or is used, irrespective of whether such description is specifically identified as method disclosure.

DETAILED DESCRIPTION OF THE PRESENTLY PREFERRED EMBODIMENTS OF THE INVENTION

FIGS. 1–4 illustrate an exemplary embodiment of an intraoral appliance 10 according to one embodiment of the instant invention. Appliance 10 comprises a formed body 12, which may be molded from such suitable biocompatible materials as polyurethane or polycarbonate plastic, among others. Body 12, thus, in this exemplary embodiment, is a unitary, generally rigid structure. In an alternative embodiment, body 12 is an assembly of various structural elements forming the parts of body 12 as described hereinbelow, the individual elements being molded or otherwise formed independently from one another and then bonded together to form body 12.

Figure 1:
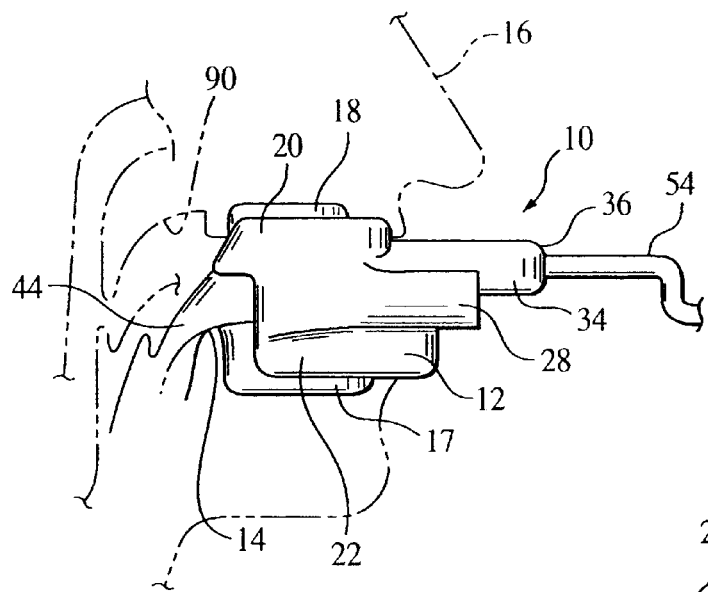
FIG. 1 is a side elevation of an intraoral apparatus according to one embodiment of the present invention showing the position of such apparatus in the oral cavity of a user.
Figure 2:
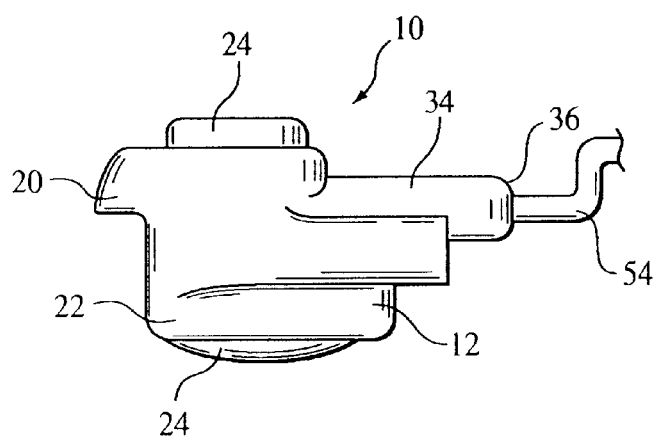
FIG. 2 is a side elevation of the intraoral apparatus of FIG. 1.
Figure 3:
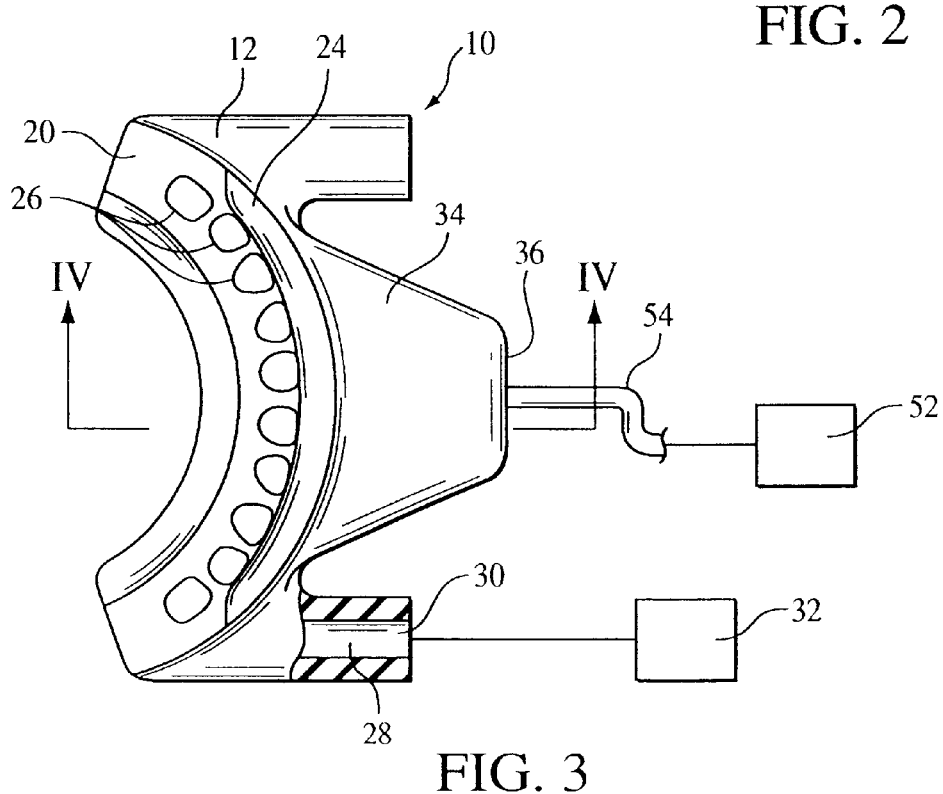
FIG. 3 is a top plan view, partially in section, of the intraoral apparatus of FIG. 1.

As shown in FIG. 1, intraoral appliance 10 is received within an oral cavity 14 of a user 16 and is retained therein by interfitting with the user's lower dentition 17 and upper dentition 18. Accordingly, body 12 includes respective lower and upper dentition receiving trays 22 and 20 shaped to conform generally to a user's lower and upper dentition, respectively. In an exemplary embodiment, each dentition receiving tray 20 and 22 carries therein a quantity of impression forming material 24, such as that used in custom fitted athletic mouth guards. One such material is ethylene vinyl acetate (EVA), which has suitable thermoplastic properties for use in a so-called "boil and bite" oral apparatus. Appliance 10, thus, can be heated in hot water or by similar means to render the EVA temporarily pliable. The user then bites into material 24 in upper and lower trays 20 and 22 to form exact impressions 26 of the user's dentition. Upon cooling or setting, the EVA retains the dentition impression 26, thereby creating a custom fitted appliance 10. It can be understood that if the impression forming material is not a thermosetting material, as described above, other conventional materials and techniques can be used to cause the material to be cast or set to the shape of the user's dentition.

In another embodiment of the present invention, dentition receiving tray 20 and 22 do not mold to match the patient's teeth. Instead, the trays, or a portion thereof, correspond, in general, to the shape of a human teeth pattern and function as a bite block. The present invention also contemplates that the body member contacts the sides of the teeth or that the body member engages or contacts the patient's gum tissue or other anatomical features. This latter configuration is especially relevant for patients who may be missing some or all of their teeth.

Of importance in the present invention is not the specific manner in which body member 12 engages or contacts the teeth or other intraoral features, but that the body member sufficiently engages or contacts the teeth or other intraoral features so as to perform the functions described herein. For example, in a further embodiment described below with respect to FIGS. 18 and 19, the present invention contemplates that the body member, or its equivalent, not contact an intraoral feature of the patient, but secures to the patient by contacting the facial region of the patient proximate to the mouth.

Referring again to FIGS. 1, 2, and 4, in a preferred embodiment of the present invention, lower dentition tray 22 is provided in a fixed position relative to upper dentition tray 20. Furthermore, lower tray 22 is offset in an anterior or forward direction, i.e., toward the right in FIGS. 1, 2 and 4, relative to the position of upper tray 20, so that when the user's upper and lower dentitions are engaged within the upper and lower dentition trays, respectively, the lower dentition and corresponding structures, including the jaw or mandible, are disposed forward of their neutral position with respect to the upper dentition. In one preferred embodiment of the invention, upper and lower dentition trays 20 and 22 are positioned such that the user's lower teeth are aligned "edge to edge" with the upper teeth, rather than residing behind or posterior to the upper teeth as is typical when the dentition is in the neutral position. In other embodiments of the invention described below, the relative position in the anterior to posterior direction of the lower dentition tray 22 with respect to upper dentition tray 20 is selectively adjustable.

In the illustrated embodiment, body 12 also includes at least one port or passage 28 defined therein with an opening 30 to permit a flow of breathing gas from a source 32 of breathing gas (FIG. 3) to be delivered via opening 30 into the intraoral cavity, and thence to the upper airway of the user. Source of breathing gas 32 may be, for example, a CPAP apparatus, a bi-level pressure support device, an auto-titration pressure support device, an oxygen concentrator, a tank of gas, or any similar apparatus suitable for providing a flow of breathing gas at a pressure as a therapeutic treatment for a breathing disorder, such as OSA, hypopnea, and UARS. An example of a suitable bilevel device that administers a flow of breathing gas a pressure that varies with the patient's respiratory cycle, is the BiPAP® family of devices manufactured by Respironics, Inc. of Pittsburgh, Pa. As the art is replete with descriptions of such CPAP, bi-level, and auto-titration pressure support devices, as well as other pressure support devices, further detailed description of source 32 is believed unnecessary for an understanding of the present invention.

Figure 6:
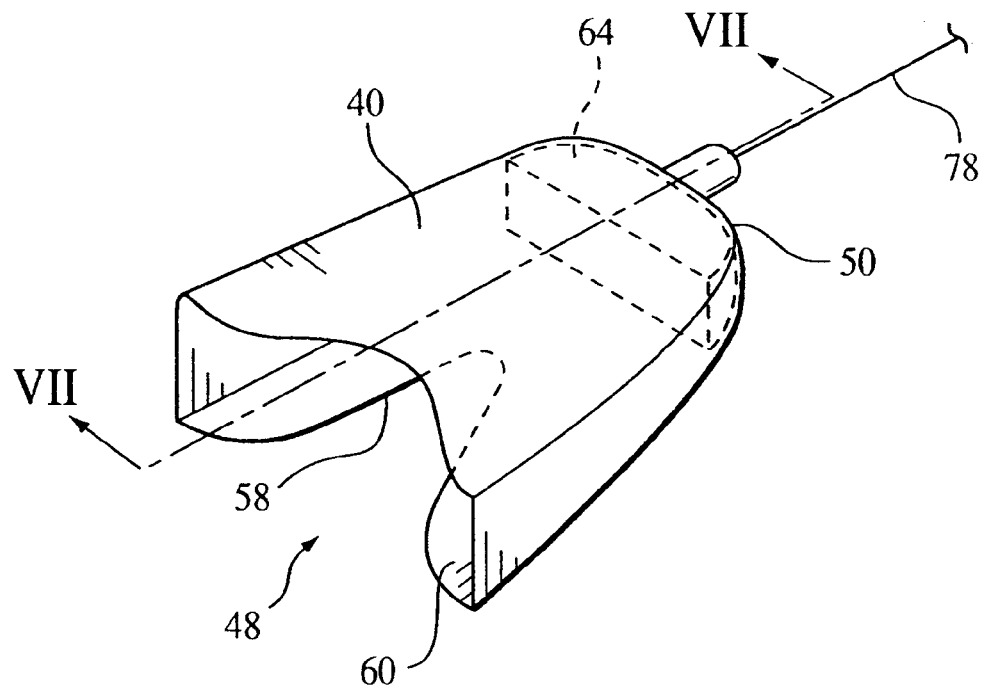
FIG. 6 is a perspective view of a tongue receiving sleeve for use with the intraoral apparatus of FIGS. 1–5 according to the principles of the present invention.
Figure 7:
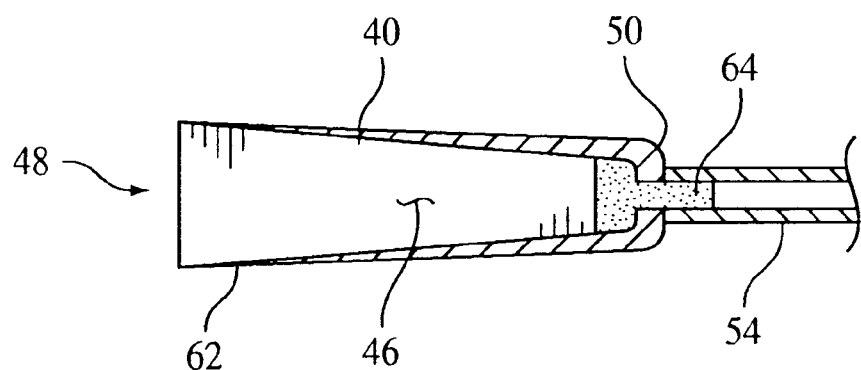
FIG. 7 is a side sectional view of the tongue receiving sleeve of FIG. 6 taken on line VII—VII of FIG. 6.

Appliance 10 further includes a tongue retaining sleeve housing 34, which in the embodiment illustrated in FIGS. 1–4, has a closed top, bottom and side walls and a closed outer end 36 to define an interior cavity 38. In the illustrated embodiment, tongue retaining sleeve housing 34 is formed as a unitary structure that is formed either integrally with appliance 10, or as a separate apparatus and affixed thereto during the assembly process. A tongue receiving sleeve 40, which is formed from, for example, a very thin, flexible polyurethane material or any suitable equivalent, as described in greater detail below with reference to FIGS. 6–7, is disposed in interior cavity 38 of sleeve housing 34.

Figure 4:
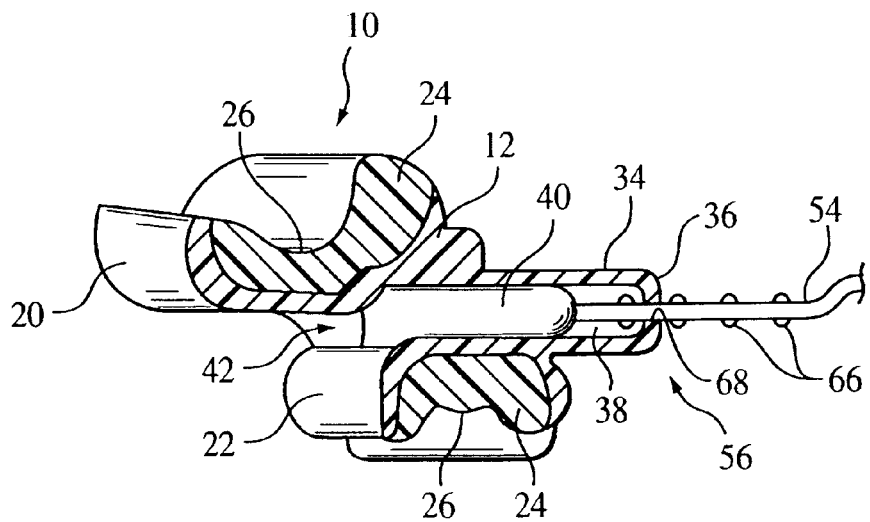
FIG. 4 is a side sectional view of the intraoral apparatus of FIGS. 1–3 taken on line IV—IV of FIG. 3.

As shown in FIG. 4, tongue receiving sleeve housing 34 is open in the posterior direction, between the upper and lower trays 20 and 22, as indicated by arrow 42. Tongue receiving sleeve 40 is adapted to fit within interior chamber 38 of tongue retaining sleeve housing 34 so as to receive a user's tongue 44, as shown in FIG. 1. An interior 46 of tongue receiving sleeve 40 is also open in the posterior direction, as generally indicated at 48 in FIGS. 6 and 7, so that a portion of the user's tongue is disposed within interior 46 of sleeve 40 through opening 48 during use of the intraoral appliance. External access to interior 46 of tongue receiving sleeve 40 is also provided at an anterior portion 50 of the sleeve so that a vacuum source 52 can be connected to interior 46 of sleeve 40. Preferably, a flexible conduit 54 coupled to vacuum source 52 applies at least a partial vacuum within interior 46 of sleeve 40, thereby collapsing sleeve 40 about the user's tongue to grip the tongue during use of the intraoral appliance.

Tongue retaining sleeve 40 is maintained in position relative to body 12 by a connecting assembly, generally indicated at 56. In a preferred embodiment of the present invention, connecting assembly 56 is used to apply an outward pulling or tension force to tongue receiving sleeve 40, thus, drawing out and retaining tongue 44 in a position advanced forwardly from a normal position of the tongue relative to the upper dentition. Details of connecting assembly 56, as used to connect tongue receiving sleeve 40 to body 12 in a manner so as to control the position of the tongue relative to the upper dentition are discussed below.

The material of tongue receiving sleeve 40 has structural properties that enable it to readily collapse about the user's tongue with application of even a very slight vacuum within interior 46. That is, tongue receiving sleeve 40 has no structural properties that tend to resist its deformation and collapse under application of an internal vacuum. A suitable material for the walls of sleeve 40 is an EVA material, polyurethane, or silicon, for example, of suitable flexibility and section thickness that it will readily collapse and seal about the user's tongue when a partial vacuum is applied within interior 46.

Preferably, tongue receiving sleeve 40 is shaped to conform to the structures of the user's oral cavity. For example, in the illustrated embodiment, sleeve 40 includes a cutout 58 on a lower wall 60 for receiving the user's frenulum, which is the web-like tissue connecting the tongue to the floor of the oral cavity, when tongue receiving sleeve 40 is positioned on the user's tongue. In addition, in the illustrated embodiment, the thickness of the walls of tongue receiving sleeve 40 varies over the length thereof, with the thinnest material being disposed at a posterior portion 62, to maximize the flexibility of the sleeve at its posterior portion, so that it too collapses about and seals against the user's tongue in response to even the slightest pressure differential between the vacuum applied within interior 36 and the pressure within the user's oral cavity.

Tongue receiving sleeve 40 includes a base element 64 at anterior portion 50 to provide a framework for supporting the flexible walls of the sleeve and for providing an interconnection between the interior of the sleeve and the vacuum source. Base element 64 preferably has a suitable degree of porosity to permit dispersion of the forces evolved as a result of the vacuum applied within the interior 46 of sleeve 40 as above described. Such porous materials are commercially available, one source being Porex Technologies of Fairbum, Ga. The porosity, as well as the described collapsing character of the walls of tongue retaining sleeve 40 when a vacuum is applied therein, contribute to increased user comfort and compliance by reducing localized stress concentrations on the tongue tissue.

As noted above, connecting assembly 56 is used to apply an outward pulling or tension force to tongue receiving sleeve 40, thus, drawing out and retaining tongue 44 in a position advanced forwardly from a normal position of the tongue relative to the upper dentition. The present invention contemplates accomplishing this function using a variety of techniques. An exemplary embodiment of one such technique is illustrated in FIG. 4.

According to this embodiment, a number of locking elements 66 are provided on the flexible conduit 54, and body 12 includes a locking aperture 68 at closed outer end 36. Each locking element 66 is independently cooperable with locking aperture 68 on body 12 for locking flexible conduit 54 in one of the plurality of discrete relative positions. Accordingly, the locking aperture is to be suitably formed to prevent pinching or constricting of flexible conduit 54 when locked. A similar locking element and locking aperture slot retention/adjustment structure is known for cable ties or hang tag retainers, such as used in retail merchandising. Locking elements 66 thus will lock into locking aperture 68, but may pass therethrough upon application of a sufficient force to permit selective adjustment of tongue retaining sleeve 40 by selecting the locking element to be locked into the locking aperture. This adjustment apparatus provides a plurality of discrete relative adjustment positions.

Although FIG. 4 illustrates the locking element being provided on flexible conduit 54, it is to be understood that a separate protruding element can be provided for carrying locking elements 66. It is to be further understood that locking elements 66 and locking aperture 68 can have a variety of configurations and sizes so long as the above-described tongue position controlling function is accomplished. Furthermore, the present invention contemplates eliminating the locking elements in favor of sizing conduit 54 and aperture 68 such that a degree of friction exists therebetween to hold tongue retaining sleeve 40 in place within housing 34, with the amount of friction being large enough to prevent movement of sleeve 40 during use, but small enough to allow the user to alter the position of the sleeve relative to the body member.

The combination of jaw and tongue positioning provides two modes of airway stabilization which, combined with positive airway pressure, is believed to afford a particularly suitable combination of interventions for the prevention of airway obstruction in many patients while offering a high degree of patient compliance. In particular, it appears that positioning the mandible with the upper and lower teeth in an "edge-to-edge" orientation often provides at least a mildly effective upper airway stabilization effect with minimal possibility of temporomandibular joint pain or dysfunction.

Figure 5:
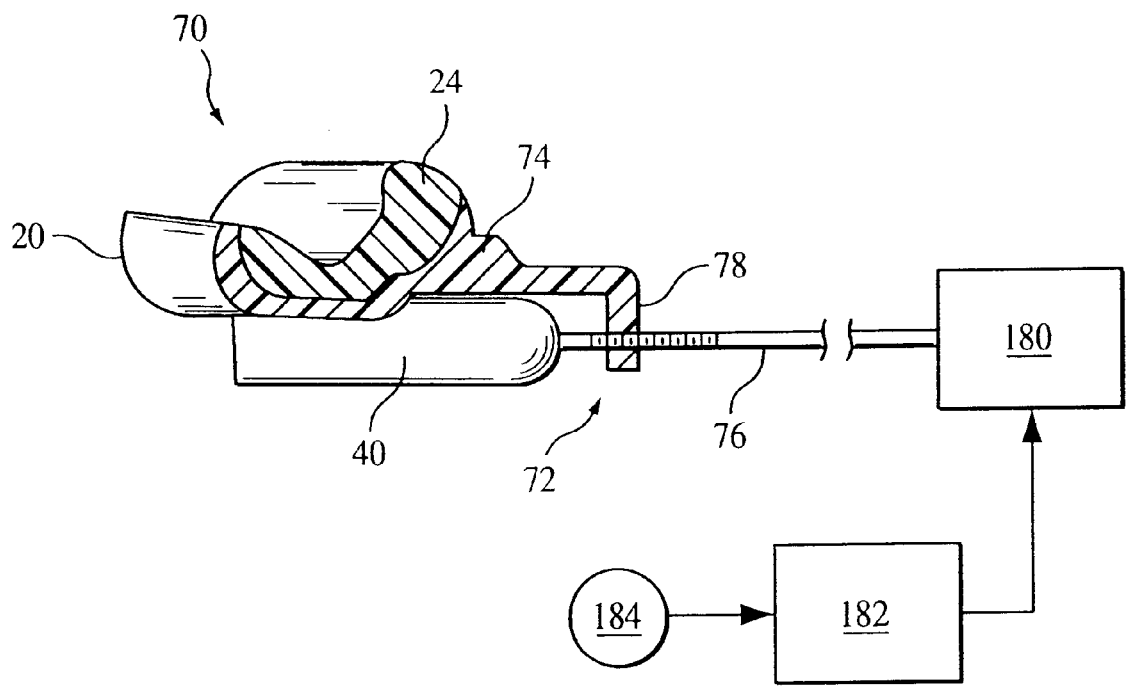
FIG. 5 is a side sectional view, similar to FIG. 4, showing a second embodiment of the intraoral apparatus according to the principles of the present invention.

In the invention described thus far, the user's mandible structure (lower dentition) and tongue are positioned and retained forwardly of their relaxed or neutral positions. If only tongue positioning is required, the apparatus of FIG. 4 need not include the lower dentition receiving tray 22, because the apparatus can be anchored to the upper dentition alone. FIG. 5 illustrates an intraoral appliance 70 having such a configuration according to a second embodiment of the invention. Intraoral appliance 70 also illustrates an alternative embodiment for a connecting assembly, generally indicated at 72, that is used to control the position of tongue receiving sleeve 40 relative to a body 74 of the appliance. The connecting assembly shown in FIG. 5 can be used in the other embodiments of the present invention.

In the embodiment shown in FIG. 5, a threaded protruding element 76 is coupled to tongue retaining sleeve 40 and a threaded tab 78 is coupled to body 74. The relative positional relationship of tongue receiving sleeve 40 relative to body 74 is controlled by rotation of threaded protruding element 76 within threaded tab 78. This embodiment for controlling the position tongue receiving sleeve 40 has the advantage over the embodiment shown in FIG. 4 in that it provides a continuous, rather than discrete, range of relative positions between sleeve 40 and body 74. In the embodiment of FIG. 5, threaded protruding element 76 also serves as the conduit that applies at least a partial vacuum within tongue retaining sleeve 40. It is to be understood, however that a separate threaded protruding element can be provided for engaging a threaded slot on body 74. The present invention also contemplates rotating threaded protruding element 76 via a motor 180 so that the position of the tongue can be controlled automatically or from a remote location while the patient is using the intraoral apparatus of the present invention.

Intraoral appliance 70 in FIG. 5, when positioned on the patient, fixes the position of the patient's tongue relative to the upper dentition. The lower dentition is not engaged by device of FIG. 5. The present invention, however, contemplates that intraoral appliance 70 can also be applied to the lower dentition, with the upper dentition remaining unengaged. This can be accomplished, for example, by inverting device 70 from the orientation shown in FIG. 5. Of course, minor modifications may be necessary in order for appliance 70 to engage the patient's lower dentition. Such a configuration and use of appliance 70 fixes the position of the patient's tongue relative to the lower dentition rather than relative to the upper dentition.

As will be recalled, the invention contemplates application of positive pressure in the user's upper airway, and therefore also in the user's oral cavity, as part of a treatment for OSA, hypopnea, and UARS. The pressure differential between a partial vacuum applied in interior 46 of tongue receiving sleeve 40, and the positive pressure applied within the user's oral cavity, will form a seal very precisely about the user's tongue. Because this seal is nearly completely devoid of self-supporting structural properties, the pressure forces molding it to the exterior form of the user's tongue will be experienced by the user as uniform pressure, rather than as a force or pressure concentrated at particular locations on the tongue. Avoidance of non-uniform force or pressure concentrations reduces the potential for discomfort or painful irritation of the tongue.

Figure 8:
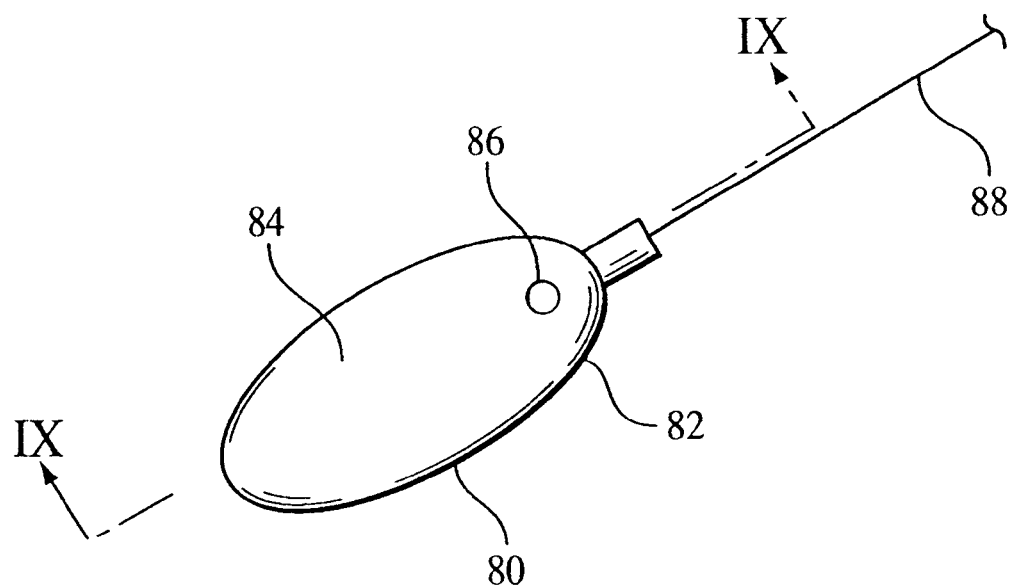
FIG. 8 is a perspective view of a soft palate engaging apparatus for use with a third embodiment of an intraoral apparatus according to the principles of the present invention.
Figure 9:
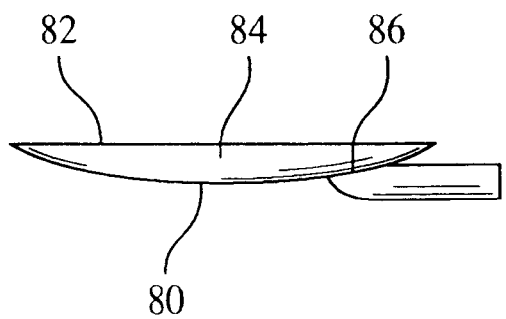
FIG. 9 is a sectional view of the soft palate engaging apparatus of FIG. 8 taken on line IX—IX of FIG. 8.

As has been noted, the invention contemplates the selective positioning of various anatomic features associated with the upper airway, including intraoral and pharyngeal features, in a manner to alleviate the incidence of airway obstruction associated with OSA, hypopnea, UARS and other conditions. Accordingly, a third embodiment of the invention shown in FIGS. 8 and 9 provides a soft palate engaging element 80, such as a suction cup or similar element, for controlling the position of the user's soft palate to treat the breathing disorder. The present invention contemplates providing soft palate engaging element 80 in addition to or in place of tongue retaining sleeve 40 in the intraoral appliance of FIGS. 1–5 so that either the tongue position controlling feature, the soft palate position controlling feature, or both can be accomplished by the intraoral appliance of the present invention. The same connecting assembly that is used to attach the tongue retaining sleeve to the body of the intraoral appliance and control the relative position thereof can be used to attach the soft palate engaging element to the body of the intraoral appliance and control the relative position thereof Soft palate engaging element 80 includes a perimeter portion 82 and a slightly hollowed or dished portion 84 within the confines of perimeter 82. An aperture or opening 86, or a porous base element (not shown) similar to that provided for the FIG. 6-7 embodiment of the tongue retaining sleeve, communicates between dished portion 84 and a suitable vacuum source (not shown) via a conduit 88.

Like the vacuum-activated, collapsing seal elements described above, soft palate engaging element 80 is formed of a material and has structural qualities such that the application of a vacuum within the confines of perimeter 82 fixes the soft palate engaging element with respect to an intraoral anatomic surface, thereby engaging perimeter 82 essentially without developing any localized force or pressure concentrations that could produce the discomfort of soft palate tissue irritation. Soft palate engaging element 80, thus, is employed by suction attachment to soft palate tissue generally at location 90, as shown in FIG. 1, to move, distend, or position the soft palate tissue in a selected manner, and preferably in a forward or anterior direction, for alleviation of airway obstruction.

Figure 10:
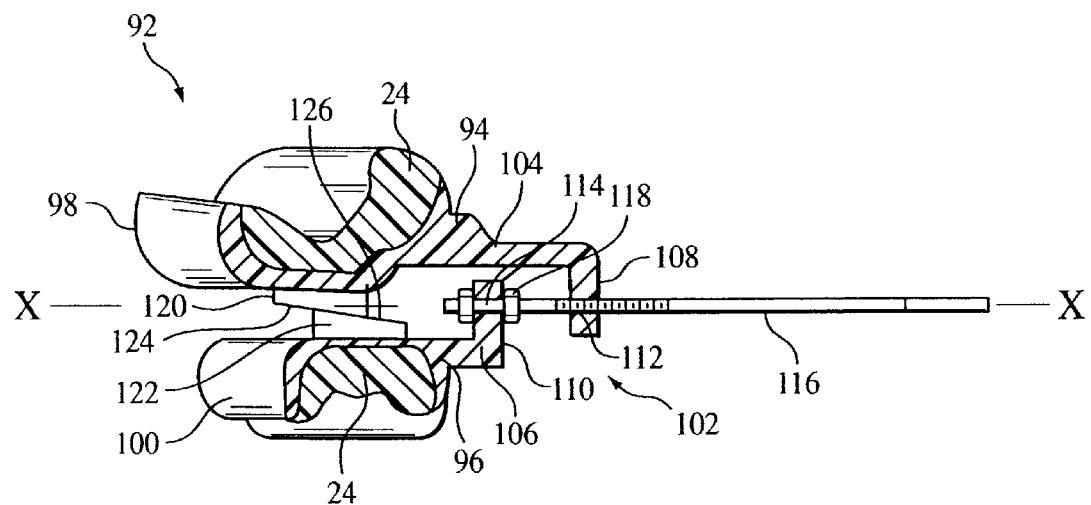
FIG. 10 is a side sectional view of a fourth embodiment of an intraoral apparatus according to the present invention showing a mandibular adjustment structure.

In the embodiments described above, and, more specifically, in the embodiment described above with respect to FIGS. 1–4, the user's upper and lower dentitions are maintained in a fixed position relative to one another and cannot be altered or changed. The present invention, however, contemplates selectively adjusting the relative positions of the upper and lower dentitions, either for patient comfort or for additional therapeutic benefits. To this end, FIG. 10 illustrates a fourth embodiment of an intraoral apparatus 92 having a mandibular adjustment function and structure for accomplishing same. The present invention contemplates that the mandibular adjustment feature of intraoral appliance 92 can be provided in conjunction with one or more of the following: (1) providing a positive airway pressure to the airway of the patient; (2) providing the tongue positioning function associated with the embodiment of FIGS. 1–7; and (3) providing the soft palate positioning function associated with the embodiment of FIGS. 8–9.

Intraoral apparatus 92 includes an upper body member 94 and a lower body member 96, each having a respective one of an upper dentition tray 98 and a lower dentition tray 100. Upper and lower body members 94 and 96 are moveable relative to one another to control the position of the user's lower dentition relative to their upper dentition. A connecting assembly, generally indicated at 102, couples the upper and lower body members and provides selective adjustment of a relative positional relationship between the upper body member and the lower body member. In the illustrated embodiment, connecting assembly 102 is a rotary screw system that provides a continuous range of positions for the lower body member relative to the upper body member or vice versa.

Projecting members 104 and 106 provided on upper body member 94 and lower body member 96, respectively, extend in an anterior direction to terminate in respective overlapping tabs 108 and 110. Respective bores 112 and 114 defined in tabs 108 and 110 are coaxially aligned to receive a threaded adjuster rod 116. Rod 116 is received within bore 114 and bushings 118 are affixed to adjuster rod 116 snugly on either side of tab 110 to thereby permit rod 116 to rotate freely within bore 114 while being axially retained with respect to tab 110.

Threads formed on adjuster rod 116 mate with corresponding threads formed within bore 112 so that upper body member 94 moves axially with respect to lower body member 96 upon rotation of adjuster rod 116. Accordingly, by selective axial rotation of adjuster rod 116, upper and lower body members 94 and 96 are selectively movable with respect to each other. Lower dentition tray 100 thus is adjustable in an anterior or posterior direction with respect to upper tray portion 98, thereby permitting selective adjustment of the user's mandible in the anterior and posterior directions, i.e. along axis x—x of FIG. 10. Moreover, this adjustment can be made manually or via a motor coupled to adjuster rod 116, and this adjustment can be made while the apparatus is being worn by the patient.

The mandibular adjustment apparatus of FIG. 10 further contemplates ramp structures 120 and 122 carried by upper and lower body members 94 and 96, respectively. Ramps 120 and 122 have mutually engaging inclined surfaces 124 and 126 that slide upon one another in response to adjustments made through rotation of adjuster rod 116 as described above. The inclined surfaces 124 and 126 are oriented so that each increment of movement of lower body member 96 in a forward or anterior direction with respect to upper body member 94 also produces a corresponding increment of increased vertical separation between upper body member 94 and lower body member 96. On the other hand, relative adjustment of lower body member 96 in a posterior direction with respect to upper body member 94 produces a corresponding increment of decreased vertical separation between upper and lower body members 94 and 96. The result is that the adjustments available with the FIG. 10 embodiment always produce movements of the mandible, with respect to the rest of the user's oral cavity anatomy, in an anterior and downward direction, or in a posterior and upward direction. It is to be understood that ramps, 120 and 122 are optional and need not be provided if movement of the mandible in an upward or downward direction are not desired.

In another aspect of the mandibular adjustment device shown in FIG. 10, adjuster rod 116 may be retained within bore 114 with sufficient free play to allow lower body member 96 limited freedom of movement with respect to upper body member 94. This freedom allows for a range of relative pitch, yaw and roll movement of lower body member 96 about the X axis with respect to upper body member 94, to thereby accommodate asymmetrical mandible movement during adjustment of its position as described above. This free play can be provided in embodiments with or without ramps 120 and 122. Furthermore, the described free play can be provided in conjunction with the action of ramps 120 and 122 to provide a limitation on the minimum vertical separation between the user's upper and lower dentition.

Although a rotary screw configuration is shown in FIG. 10 for moving the upper and lower body members relative to one another, it is to be understood that other mechanisms for adjusting the position of the lower body member relative to the upper body member are contemplated by the present invention. For example, the locking element and locking aperture configuration illustrated in FIG. 4 can be used to selectively set the position of the lower body member relative to the upper body member.

Yet another embodiment of a mandibular adjustment apparatus 125 is shown in FIGS. 11–14. As with the apparatus of FIG. 10, the function of selectively setting the position of the lower dentition relative to the upper dentition can be provided in combination with one or more of the above-discussed functions: (1) the application of a positive pressure therapy, which is believed to allow a reduced pressure to be provided to the patient; (2) the tongue positioning function associated with the embodiment of FIGS. 1–7; and (3) the soft palate positioning function associated with the embodiment of FIGS. 8–9.

Mandibular adjustment apparatus 125 includes an upper body member 127 and a lower body member 128 adapted to receive the user's upper and lower dentitions, respectively. The present invention contemplates that upper and lower body members 127 and 128 are similar in material and construction to the corresponding elements 20 and 22 in FIG. 4 or corresponding elements 94 and 96 in FIG. 10. However, upper and lower body members 127 and 128 are shown schematically in FIG. 11 for convenience of illustration. A connecting bias assembly 130 connects upper body member 127 with lower body member 128 and includes a biasing spring 132 having an elongated C-shape, a connection 134 connecting one end of the spring 132 to body member 128, and a ratcheting adjustment assembly 136 connecting the opposed end of spring 132 to body member 127. Preferably, two bias assemblies 130, which are spaced from each other in a lateral direction, for example, by being located on adjacent laterally opposed sides of the body members 127, 128, are provided for connecting the upper and lower body members.

Connection 134 may be, for example, a snap-fit button connection to allow pivotal movement of spring end 138 with respect to the associated body member. In addition to pivotal movement, connection 134 preferably provides sufficient freedom to accommodate differential vertical movement between opposed sides of the apparatus of FIG. 11, such as would occur if one of body members 127 or 128 moves in differential rolling or yawing motion with respect to the other, about an axis extending in the anterior to posterior direction, or to the right and left in FIG. 11. Alternatively, this freedom can be provided by differential flexing of spring elements 132, and attendant torquing or twisting of the spring elements.

Figure 11:
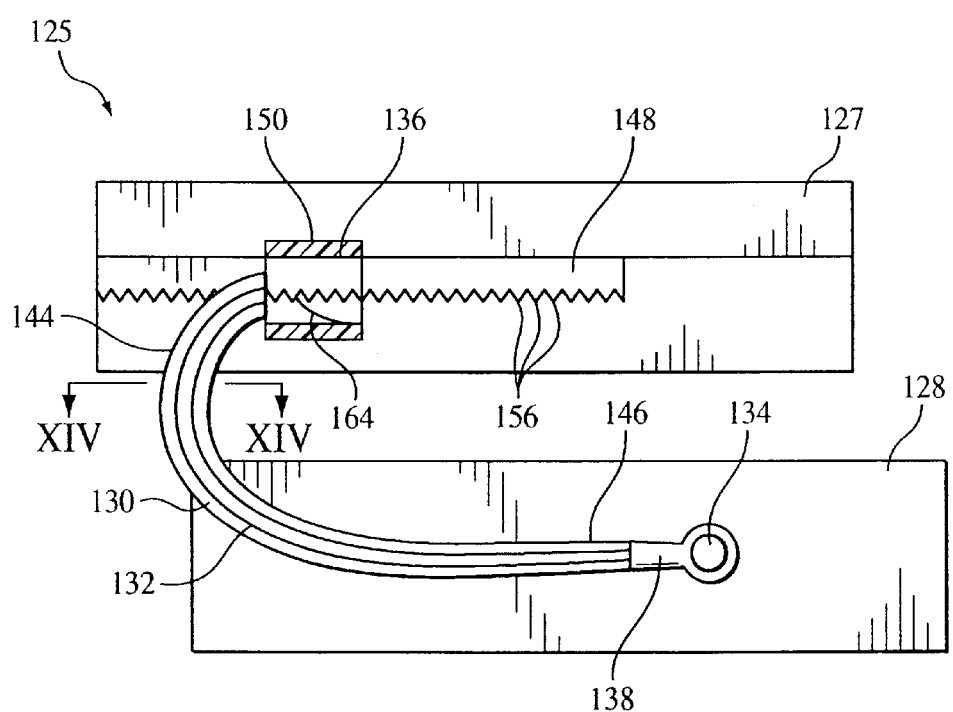
FIG. 11 is a side view showing a further embodiment of the mandibular adjustment structure.
Figure 14:
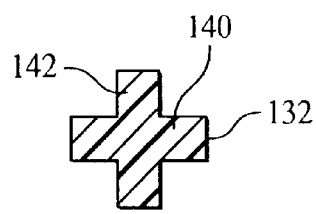
FIG. 14 is a cross-sectional view taken on line XIV—XIV of FIG. 11.

Spring 132 may be molded by any suitable molding process to have any of a variety of cross sectional forms, for example, a pair of flat, intersecting web elements 140, 142 forming the unitary spring 106 as shown in FIG. 14. In addition, in the illustrated embodiment, spring 132 tapers in cross sectional size from the larger cross section portion 144 thereof to a smaller cross section portion 146, as shown in FIG. 11. This tapered form allows the spring to exert sufficient bias for its intended purpose, as described hereinbelow, in a horizontal direction, while exerting substantially less bias to resist relative vertical movement. This permits the apparatus to be used for biasing the mandible or jaw, engaged by lower body member 128, outward or toward the right in FIG. 11 with respect to the position of the upper dentition, engaged by upper body member 127. The vertical flexibility of spring 132 readily accommodates relative vertical movement between upper body member 127 and lower body member 128 without significant resistance, even while applying the bias which urges lower body member 128 forwardly of upper body member 127.

Ratchet adjustment assembly 136 permits adjustment of upper body member 127 with respect to lower body member 128 to a plurality of discrete relative positions in the anterior-posterior direction for the same purposes as described hereinabove with reference to other embodiments, such as FIG. 10. However, for the embodiment of FIG. 11, adjustment of the ratchet adjustment assembly 136 will have the effect of increasing or decreasing the biasing force of spring 132 as it urges the user's mandible outwardly, that is to the right in FIG. 11. Spring 132 also provides flexibility that allows relative movement of the restrained intraoral structures to positions intermediate adjacent discrete positions of ratchet 136. Hence, this adjustment apparatus provides aspects of both discrete and continuous adjustment.

Figure 12:
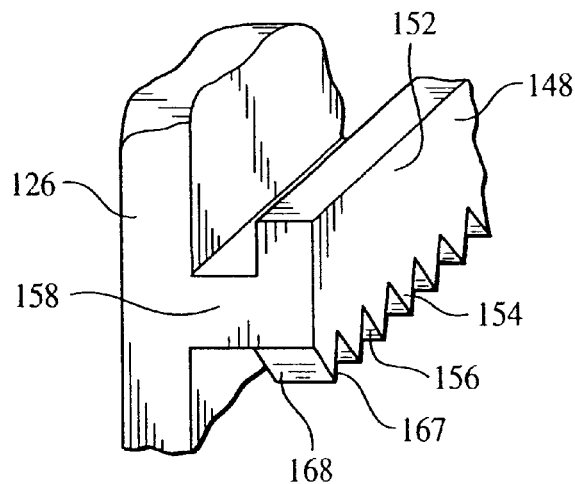
FIG. 12 is a perspective view of a portion of the intraoral apparatus of FIG. 11.

Ratchet adjustment assembly 136 includes a ratchet rack 148 carried by upper body member 127 and a ratchet engaging cog assembly 150 for adjustably engaging rack 148. Referring to FIG. 12, ratchet rack 148 comprises an upwardly projecting rail portion 152, a downwardly projecting ratchet rack portion 154 having a plurality of longitudinally spaced ratchet teeth 156, and a longitudinally extending web portion 158, all formed as an integral structure and also preferably integral with upper body member 127.

Figure 13:
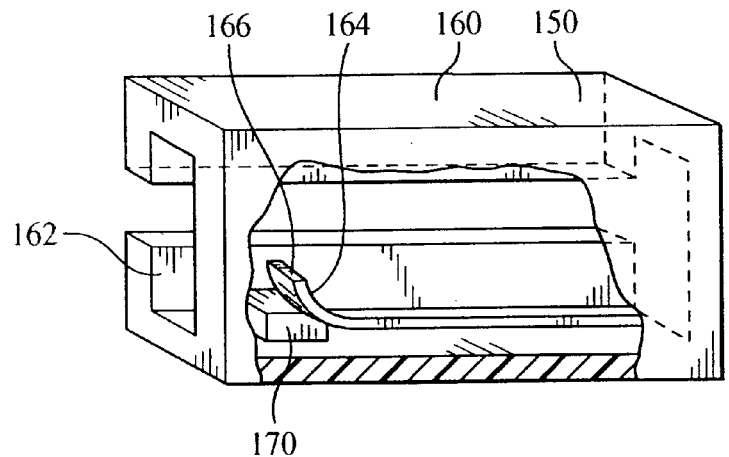
FIG. 13 is a perspective view, partially broken away, of a portion of the apparatus of FIG. 11.

Ratchet engaging cog assembly 150 is fixed, preferably integrally, to the end of spring 132 opposite connection 134, as shown in FIG. 11. Referring to FIG. 13, ratchet engaging cog assembly 150 includes a formed body member 160 having generally a C-shape and thus defining a channel 162 extending therethrough. Channel 162 is of a form to receive the ratchet rack 148 therein in a manner that body member 160 encloses and captures ratchet rack 148 and is slideable longitudinally thereof.

A ratchet tooth engaging cog element 164 is fixed within channel 162 and includes a ratchet tooth engaging end 166 that projects upwardly into interfering relation with ratchet teeth 156. Cog element 164 may be of spring steel, for example, or plastic, or any suitable material having the property of flexibility and spring biasing so that it will override individual ratchet teeth 156 as body member 160 is moved along ratchet rack 148 in the forward or anterior direction, but will spring upward upon passing each ratchet tooth 156 to thereby preclude sliding movement of body member 160 in the opposite direction. Of course, in order to operate as described, the face angles of ratchet teeth 156 must be properly formed. In the embodiment shown, ratchet teeth 156 preferably have a generally vertical face 167 against which the engaging end 166 of cog element 164 abuts, and a confronting face 168 that sets at an acute angle to the vertical to provide clearance for the upwardly projecting engaging end 166 of cog 164. See FIG. 12.

As shown in FIG. 13, engaging end 166 of cog 164 may be held in an interfering position with respect to ratchet teeth 156 by a block 170 or similar structure underlying cog element 164 and thereby maintaining end 166 thereof in an elevated position. Alternatively, cog element 164 may be biased to project upwardly on its own, without assistance such as provided by block 170.

The apparatus of FIGS. 11–14 is used to provide adjustable upper and lower dentition engaging member for all of the purposes described hereinabove for such an adjustable apparatus and operates as follows. The adjustment of relative position between upper body member 127 and lower body member 128 is effected by sliding ratchet engaging cog assembly 150 onto the left end of ratchet rack 148, as reckoned in FIG. 11, and moving cog assembly 150 along rack 148 as ratchet tooth engaging cog element 164 overrides successive ratchet teeth 156 until the desired relative position of upper and lower body elements 127 and 128 is obtained. The position will be the one which provides the desired relative position of the user's mandible with respect to the upper dentition, and the desired biasing of spring 132 to maintain the mandible in the selected relative position. It will be appreciated that the further one slides element cog assembly 150 along rack 148 in the anterior direction or to the right in FIG. 11, the greater the bias of spring 132 urging lower body member 128 in the same direction with respect to upper body member 127. If, during the adjustment process, one moves cog assembly 150 past the desired adjustment position, one need only slide element 132 to the right and completely off of rack 148, reassemble the elements as described above, and perform the adjustment process again.

The apparatus of FIGS. 11–14 may be of any suitable material, preferably molded plastic material similar to the materials suggested above for components of other similar embodiments.

The invention as described hereinabove includes an apparatus for positioning various anatomic features associated with the upper airway, in conjunction with the application of positive airway pressure. Specifically, it has been long recognized that positive airway pressure may be employed to splint the upper airway and thereby prevent airway collapse which results in airway obstruction. The present invention contemplates the positioning of one or more anatomic features associated with the upper airway, or the same in combination with application of positive airway pressure, to alleviate airway obstruction. In one embodiment, the described apparatus is employed to position the user's mandible in a forwardly protruding position with respect to its neutral position. Such positioning of the mandible tends to draw forward adjacent intraoral tissue, including tissue adjacent to the upper airway and other pharyngeal and peri-pharyngeal tissue and structures. By thus positioning such tissue, it is possible to stabilize portions of the upper airway which, if left in an unstabilized state, could contribute to the occurrence of airway obstruction. The additional airway stabilization may accord such benefits as the ability to completely control airway collapse with a reduced magnitude of positive airway pressure.

The method of the invention further contemplates maintaining the tongue in a position displaced in the anterior direction from its usual rest or neutral position, alone or in combination with positive airway pressure. This is another mode of stabilization for tissue in or adjacent to the upper airway that can beneficially reduce the incidence of airway collapse due to airway instability. The use of such tongue positioning in conjunction with positive airway pressure thus affords the prospect for beneficial treatment similar to that available through the combination of jaw or mandible positioning and positive airway pressure. As such, the invention also contemplates combining tongue and mandible positioning with positive airway pressure to alleviate airway obstruction.

Similarly, the method of the invention also contemplates soft palate tissue positioning, such as by use of the soft palate engaging element 80. Drawing the soft palate tissue in an anterior direction can help stabilize the upper airway, thereby reducing the incidence of airway obstruction. The described soft palate positioning and/or tensioning also may be employed in combination with positive airway pressure.

Still further, the method elements of mandible positioning, tongue positioning and soft palate positioning may be employed in any combination, with or without positive airway pressure, to provide airway stabilization.

Once the optimal positions of the respective intraoral, pharyngeal, or other upper airway anatomic features have been determined for the specific patient, the apparatus configurations that result in the optimal positions are recorded. For example, suitably numbered index marks (not shown) provided on adjacent, relatively movable portions of the apparatus of FIG. 10 may be employed to indicate the relative position of the elements 94 and 96 of that apparatus. An entirely similar scheme may be employed to identify and record the optimal positions for a tongue retaining apparatus and/or a soft palate retaining apparatus as above described, whether using the FIG. 4 locking element mechanism, the FIG. 5 screw adjustment mechanism, the FIG. 11-14 rack and ratchet mechanism, or any suitable alternative adjustment scheme. The index readings are recorded, and from them, a permanent apparatus of proper configuration is fabricated for the specific patient.

In the embodiments discussed above, the position of the tongue (FIGS. 1–5), soft palate, (FIGS. 7–8), and mandible (FIG. 10), or any combination thereof, is controllable a motor rotating an actuating rod, such as threaded protruding element 76 in FIG. 5 and adjuster rod 116 in FIG. 10. The present invention further contemplates that the operation of the motor can be controlled either manually or automatically to achieve a desired anatomical position. For example, FIG. 5 illustrates a motor 180 that drives rod 76 for moving sleeve 40 relative to tray 20. A controller 182, such as a microprocessor, controls the actuation of motor 180 to control the position of sleeve 40 relative to tray 20. Of course, this same configuration can be used to control the position of the soft palate and mandible or any combination thereof.

In an exemplary embodiment of the present invention, controller 182 controls the position of the patient's anatomical features according to a prescribed or preset positioning algorithm. For example, the tongue, soft palate, mandible or any combination of these features can be maintained in a natural or neutral position when the user first dons the intraoral appliance. Thereafter, the position of the anatomical feature can be changed over time to a position that better stabilizes the upper airway. This feature of present invention allows the patient time to fall asleep with his or her anatomical features in a neutral position. After a set or selectable period of time, controller 182 automatically varies the position of the anatomical feature associated with the upper airway, such as the tongue, soft palate, mandible, or other pharyngeal and peri-pharyngeal features, to the treatment desired position. This can be done gradually over time or after a fixed time period has elapsed; preferably a time period sufficient to allow the patient time to fall asleep.

The present invention also contemplates controlling or changing the position of the anatomical feature associated with the upper airway based on a monitored parameter. To this end, a sensor 184 is provided for communicating a signal indicative of the monitored parameter to controller 182. For example, the present invention contemplates that sensor 184 is a microphone and that controller 182 detects whether the patient is snoring based on the signal provided by the microphone. Upon detecting the presence of snore, controller 182 actuates motor 180 to advance the tongue outward in a direction outward from the mouth a predetermined amount. This process can continue until the maximum distended position is reached or the snore stops. If snore is not detected for a predetermined period of time, controller 182 actuates motor 180 to move the tongue in a direction toward its normal or neutral position.

It is to be understood that a variety of parameters can be monitored and used to control the position of the anatomical features of the patient to achieve the desired treatment. For example, the patient's respiration can be monitored via a flow sensor or respiratory belt as sensor 184, and the patient's anatomical features can be adjusted, if, for example, an apnea or hypopnea is detected, to alleviate or mitigate the occurrence of this disorder.

The present invention also contemplates controlling the position of the anatomical features based on the patient's ventilation rather than based on time. For example, the position of the anatomical feature can be gradually adjusted during each successive breath, or after a fixed number of breaths have been detected. That is, the position of the anatomical features can be incrementally moved every breath, or every $3^{rd}$ breath and so on, for example, until the desired therapy position is reached. This achieves nearly the same function as the timed change in position, but does so in rhythm with the activities of the patient, rather than based on a clock or other timing mechanism.

Figure 15:
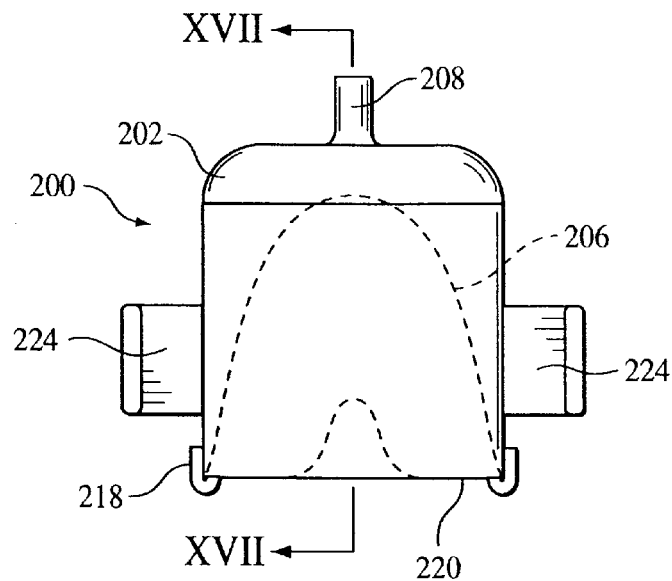
FIG. 15 is a top view of an intraoral apparatus according to fifth embodiment of the present invention.
Figure 16:
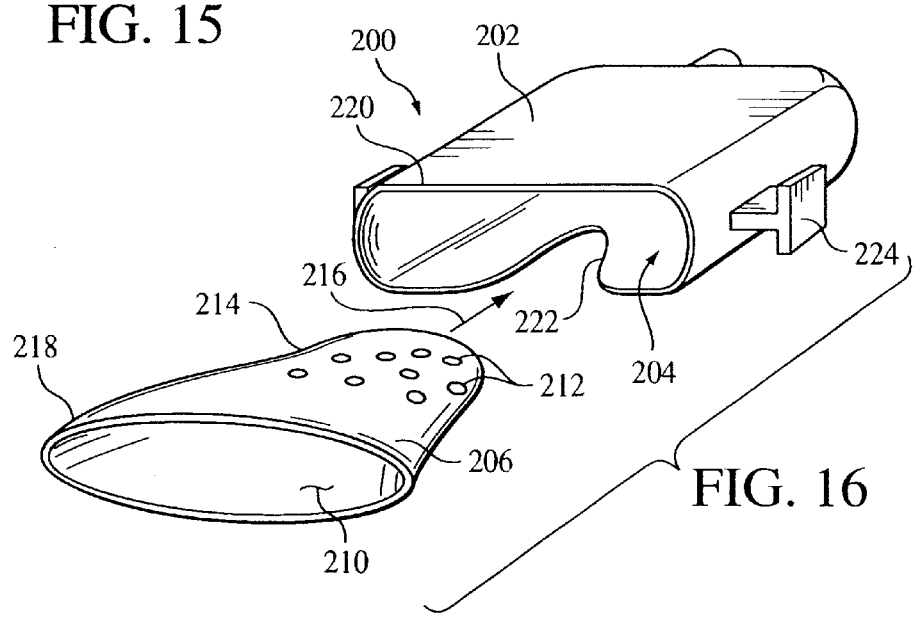
FIG. 16 is a perspective view of the intraoral apparatus of FIG. 15 illustrating the cooperation between the body member and the tongue receiving sleeve.
Figure 17:
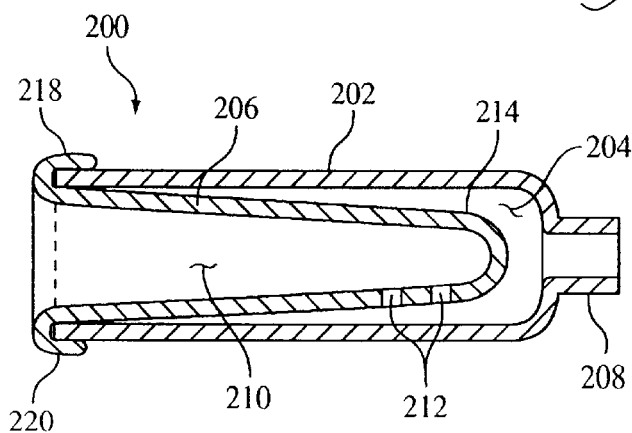
FIG. 17 is a side sectional view of the intraoral apparatus taken along line XII—XII of FIG. 15.

FIGS. 15–17 illustrate an intraoral apparatus 200 according to fifth embodiment of the present invention. Intraoral apparatus 200 includes a body member 202 with a cavity 204 defined therein for receiving a tongue receiving sleeve 206. Body member 202 is sized and configured to fit comfortably within the user's mouth. Preferably, includes a cutout 203 to allow room for the patient's frenulum.

In this embodiment, sleeve 206 is secured in cavity 204 and a vacuum or partial vacuum is supplied to the cavity. A vacuum port 208 is provided at one end of body member 202 for communicating the vacuum source to cavity 204. Body member 202 is made from a material having sufficient rigidity so that it does not collapse when a vacuum is applied in cavity 204. Sleeve 206, on the other hand, is made from the same or similar material as sleeve 40 described above, so that sleeve 206 readily collapses about the patient's tongue when a vacuum is applied to an interior 210 of the sleeve. One or more holes 212 are defined in a first end portion 214 of sleeve 206 to communicate interior 210 of sleeve 206 with cavity 204, and, hence, with the vacuum source.

Sleeve 206 inserts into cavity 204, as indicated by arrow 216 in FIG. 16, and is secured in place in cavity 204 so as to seal the end of cavity 206 opposite port 208. In the illustrated embodiment, sleeve 206 is secured in cavity 206 and seals the end thereof by overlapping a second end portion 218 of the sleeve over an end 220 of body member 202. Sleeve 206 is preferably detached from body member 202 after each use and discarded, while body member 202 can be reused. It is to be understood that the present invention contemplates other techniques for securing sleeve 206 to body member 202 while sealing one end of cavity 204. For example, a sealing ring can be provided that physically engages end portion 218 of sleeve 206 with end portion 220 of body member 202.

The purpose of sleeve 206 is to maintain a secure engagement with the patient's tongue by supplying a vacuum to interior 210 of the sleeve while maintaining a comfortable shape for the tongue. During use, the patient's tongue expands or contours to fit the shape of the sleeve as a result of the vacuum in interior 210 where the tongue is located. However, the tongue is prevented from excessive expansion by the sleeve itself. Thus, the tongue is comfortably held in place in cavity 204. The use of multiple holes or a gas permeable material in end portion of sleeve 206 allows the forces resulting from the vacuum within sleeve 206 to be widely distributed over the patient's tongue.

The present invention contemplates a variety of techniques for securing body member 202 to the patient. For example, one or more dentition trays, such as those discussed above with respect to FIGS. 1–5 can be provided for engaging the user's teeth. In the embodiment illustrated in FIGS. 15 and 16, bite blocks 224 are provided on each side of body member 202 for contacting the patient's teeth.

Figure 18:
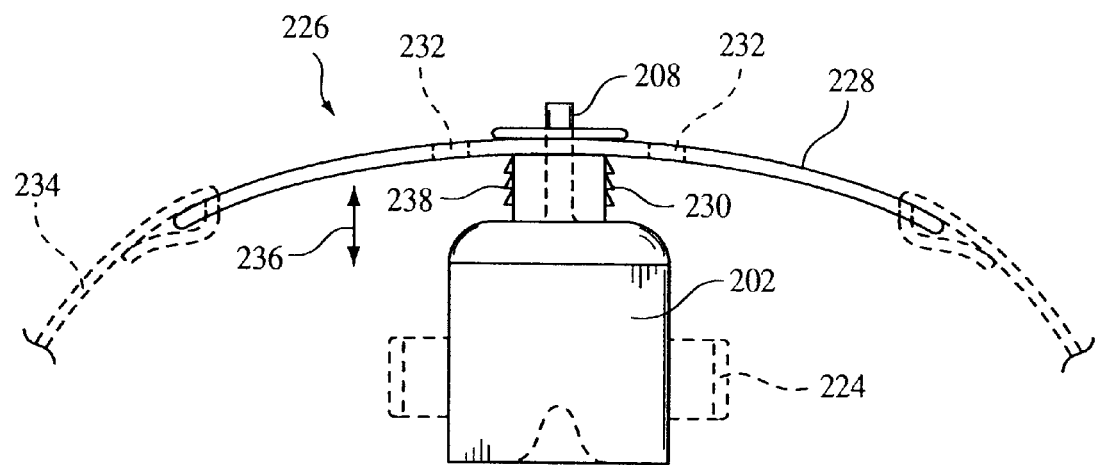
FIGS. 18 and 19 are top and front views, respectively, of an intraoral apparatus according to a fifth embodiment of the present invention showing a face engaging assembly for use in securing the intraoral apparatus to the patient.
Figure 19:
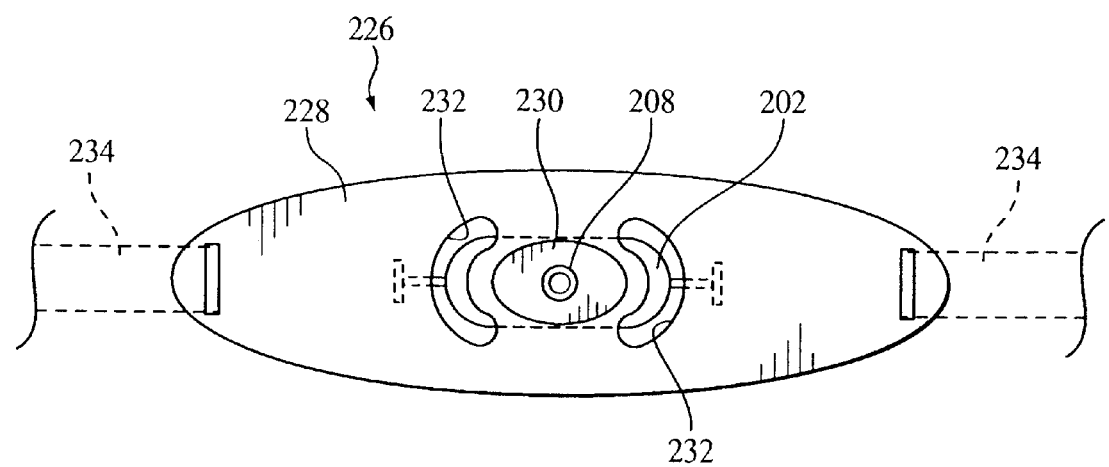

FIGS. 18 and 19 illustrate yet another technique for securing body member 202 to the patient using a face engaging assembly, generally indicated at 226. In this embodiment, a face engaging member 228 is attached to body member 202 via an attachment stem 230, which is preferably integrally formed with body member 202. Face engaging member 228 overlies the patient's face in an area proximate to the mouth to hold body member 202 in place in the user's mouth.

Face engaging member 228 preferably includes at least one hole 232 defined therethrough to allow air or other breathing gas to be delivered to the patient via the mouth. Of course, these hole can be eliminated if mouth breathing is not required.

Face engaging assembly can optionally include headgear straps 234 for securing the assembly to the patient's head. Straps 234 are secured to face engaging member 228 in any conventional manner, such as by providing slots in face engaging member 228.

In addition, the distance between face engaging member 228 and body member is preferably adjustable to allow the patient to tailor the assembly to meet their particular needs. That is, face engaging member 228 is preferably adjustable in the directions indicated by arrows 236 relative to body member 202. In the illustrated embodiment, this is accomplished by providing a plurality of barbs 238 on stem 230. The opening in face engaging member 228 through which stem 230 is inserted engages one of the barbs for maintaining the face engaging member 228 in one of selectable positions. Other techniques, such as a frictional engagement between stem 230 and face engaging member 228 member are contemplated for allowing these to components to be connected, yet moveable relative to one another. A lip is provided as the end of stem 230 to prevent disengagement of face engaging member 228 from body member 202.

As with the previous embodiments, the present invention contemplates providing a pressure support therapy in conjunction with the use of the oral appliance illustrated in FIGS. 15–19. This can be accomplished, for example, by delivering the positive pressure through the nose or through conduits (not shown) provided in the oral appliance of FIGS. 15–19. By maintaining the position of the tongue in the patient's mouth using the device of FIGS. 15–19, the present invention allows for lower positive pressure to be applied to the patient.

Although the invention has been described in detail for the purpose of illustration based on what is currently considered to be the most practical and preferred embodiments, it is to be understood that such detail is solely for that purpose and that the invention is not limited to the disclosed embodiments. In particular, any adjustment mechanism described herein may be employed with any described anatomic feature engaging apparatus, and all such combinations can provide essentially the same modes of freedom. The invention thus is intended to cover all modifications and equivalent arrangements that are within the spirit and scope of the appended claims.

What is claimed is:

1. An apparatus for enhancing patency of a user's airway comprising:
    a first member adapted to contact a portion of a user;
    a flexible sleeve adapted to be received at least partially within such a user's oral cavity and adapted to receive a portion of such a user's tongue therein, wherein the flexible sleeve is of sufficient flexibility that, during use, the flexible sleeve readily collapse about the portion of such a user's tongue upon application of a vacuum within the flexible sleeve, and wherein application of such a vacuum within the flexible sleeve fixes the flexible sleeve to the portion of such a user's tongue in the without distending such portion of a user's tongue so that a position of such a user's tongue is controllable by controlling a position of the flexible sleeve; and
    a first connecting assembly cooperable with the first member and the flexible sleeve to maintain a fixed position between the first member and the flexible sleeve during use of the apparatus.

2. The apparatus as set forth in claim 1, wherein the first member engages at least one of a user's upper dentition, lower dentition, and a facial region proximate to such a user's mouth.

3. The apparatus as set forth in claim 1, wherein the first member, the flexible sleeve, and the first connecting assembly are configured and arranged such that the fixed position is a position advanced forwardly from a normal position of a user's tongue relative to such a user's upper dentition.

4. The apparatus as set forth in claim 1, wherein the first connecting assembly is configured and arranged to provide selective adjustment of a relative positional relationship between the first member and the flexible sleeve with respect to each other to control a position of a user's tongue relative to an upper dentition.

5. The apparatus as set forth in claim 4, wherein the first connecting assembly includes a rotary screw actuated by rotation thereof for adjustment of the relative positional relationship between the first member and the flexible sleeve with respect to each other.

6. The apparatus as set forth in claim 4, wherein the first connecting assembly includes a protruding element operatively coupled to the first member and the flexible sleeve such that the flexible sleeve is selectively adjustable over a plurality of discrete positions relative to the first member by adjusting a position of the protruding element relative to the first member.

7. The apparatus as set forth in claim 6, wherein:
    (a) the protruding element is a flexible conduit used to communicate a vacuum with an interior of the sleeve and includes a plurality of spaced apart locking elements disposed thereon;
    (b) the first member includes a locking aperture; and
    (c) each locking element is independently cooperable with the locking aperture for locking the protruding element in one of the plurality of discrete relative positions.

8. The apparatus as set forth in claim 4, further comprising:
    a motor connected to the first connecting assembly for moving the flexible sleeve relative to the first member responsive to actuation of the motor; and
    a controller coupled to the motor, wherein the controller controls the actuation of the motor.

9. The apparatus as set forth in claim 8, further comprising a sensor for monitoring a parameter associated with such a user, and wherein the controller controls the actuation of the motor based on the monitored parameter.

10. The apparatus as set forth in claim 1, wherein the first member is adapted to engage a user's upper dentition, the apparatus further comprising:
    a second member adapted to engage a user's lower dentition; and
    a second connecting assembly cooperable with the second member and at least one of the first member and the flexible sleeve to maintain a predetermined relative positional relationship therebetween.

11. The apparatus as set forth in claim 10, wherein the second connecting assembly and second member are configured and arranged such that, in use, the second member retains a user's lower dentition in a position advanced forwardly from a normal position thereof with respect to such a user's upper dentition.

12. The apparatus as set forth in claim 10, wherein the second connecting assembly is configured and arranged to provide selective adjustment of a position of a user's lower dentition relative to such a user's upper dentition.

13. The apparatus as set forth in claim 12, further comprising:
    a motor connected to the second connecting assembly for moving the second member relative to the first member responsive to actuation of the motor; and
    a controller coupled to the motor, wherein the controller controls the actuation of the motor.

14. The apparatus as set forth in claim 13, further comprising a sensor for monitoring a parameter associated with such a user, and wherein the controller controls the actuation of the motor based on the monitored parameter.

15. The apparatus as set forth in claim 1, further comprising:
    a vacuum source; and
    a delivery system that communicates the vacuum source with an interior of the flexible sleeve.

16. The apparatus as set forth in claim 1, further comprising
- a passage defined through at least one of the first member and the connecting assembly, and
- a positive airway pressure source for providing positive pressure breathing gas in an upper airway of a user via the passage.

17. The apparatus as set forth in claim 1, wherein the first member includes a tongue receiving cavity adapted to receive at least a portion of the flexible sleeve, wherein a first opening is provided in the first member for communicating a vacuum source with the tongue receiving cavity, wherein a second opening is provided in the first member for disposing the flexible sleeve in the tongue receiving cavity, wherein the second opening is sealed responsive to the flexible sleeve being positioned in the tongue receiving cavity so that the vacuum can be maintained in the tongue receiving cavity, and wherein the flexible sleeve includes an opening defined therein for communicating an interior of the flexible sleeve with the tongue receiving cavity.

18. The apparatus as set forth in claim 17, wherein an end portion of the flexible sleeve engages a portion of the first member proximate to the second opening to form the seal.

\* \* \* \* \*